US006913605B2

(12) United States Patent
Fletcher et al.

(10) Patent No.: US 6,913,605 B2
(45) Date of Patent: Jul. 5, 2005

(54) MICROFLUIDIC DEVICES AND METHODS FOR PRODUCING PULSED MICROFLUIDIC JETS IN A LIQUID ENVIRONMENT

(75) Inventors: Daniel A. Fletcher, Stanford, CA (US); Daniel Palanker, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 387 days.

(21) Appl. No.: 09/683,117

(22) Filed: Nov. 20, 2001

(65) Prior Publication Data

US 2002/0045911 A1 Apr. 18, 2002

Related U.S. Application Data

(63) Continuation-in-part of application No. PCT/US00/13762, filed on May 19, 2000.
(60) Provisional application No. 60/135,827, filed on May 21, 1999.

(51) Int. Cl.[7] ............................................... A61B 17/36
(52) U.S. Cl. ............................. 606/39; 606/13; 606/41; 606/42; 606/45; 606/167
(58) Field of Search ............................. 606/167, 39, 41, 606/42, 45

(56) References Cited

U.S. PATENT DOCUMENTS

| | | | |
|---|---|---|---|
| 5,288,288 A | | 2/1994 | Lewis et al. |
| 5,871,462 A | | 2/1999 | Yoder et al. |
| 5,944,686 A | | 8/1999 | Patterson et al. |
| 6,039,726 A | | 3/2000 | Lewis et al. |
| 6,244,693 B1 | * | 6/2001 | Misumi ........................ 347/65 |
| 6,280,513 B1 | * | 8/2001 | Osumi et al. ............... 106/31.6 |

FOREIGN PATENT DOCUMENTS

| | | |
|---|---|---|
| WO | WO 98/12974 | 4/1998 |
| WO | WO 99/33510 | 7/1999 |

OTHER PUBLICATIONS

Palanker, et al., "Dynamics of ArF Excimer Laser–induced Cavitation Bubbles in Gel Surrounded by a Liquid Medium," Lasers in Surgery and Medicine, 21:294–300, 1997.
Palanker, et al. "Electric discharge–induced cavitation: A competing approach to pulsed lasers for performing micro-surgery in liquid media," Proceedings of the SPIE, vol. 2975, pp. 351–360.
Van Leeuwen, et al., "Excimer Laser Ablation of Soft Tissue: A Study of the Content of Rapidly Expanding and Collapsing Bubbles," IEEE Journal of Quantum Electronics, vol. 30, No. 5, 1994, pp. 1339–1345.
Vogel, et al., "Intraocular Nd:YAG Laser Surgery: Light–Tissue Interaction, Damage Range, and Reduction of Collateral Effects," IEEE Journal of Quantum Electronics, vol. 26, No. 12, 1990, pp. 2240–2260.

* cited by examiner

*Primary Examiner*—Vy Bui
(74) *Attorney, Agent, or Firm*—Bret E. Field; Bozicevic, Field & Francis LLP

(57) ABSTRACT

Microfluidic devices and methods for their use in producing pulsed microfluidic jets in a fluid environment are provided. The subject microfluidic devices are characterized by the presence of a microfluid chamber at their distal ends. The microfluid chamber is bounded by an opening at one end, a vapor producing means opposite the opening, and side walls between the opening and the vapor producing means. The microfluid chambers are further characterized in that the only way fluid can exit the microfluid chambers is through the opening. In using the subject devices to produce a fluid jet in a fluid environment, the chamber is first contacted with the fluid environment. The vapor producing means is then actuated in a manner sufficient to produce a vapor bubble in the chamber which, in turn, produces a microfluidic jet in the fluid environment. The subject devices and methods find use in a variety of different applications, e.g., cutting tissue, introducing fluid into a cell, and the like.

35 Claims, 3 Drawing Sheets

MICROFLUIDIC DEVICES AND METHODS FOR PRODUCING PULSED MICROFLUIDIC JETS IN A LIQUID ENVIRONMENT

CROSS REFERENCE TO RELATED APPLICATIONS

This application is a continuation-in-part application of application Ser. No. PCT/US00/13762 filed May 19, 2000 and designating the United States; which application claims priority pursuant to 35 U.S.C. § 119 (e) to the filing date of the U.S. Provisional Patent Application Ser. No. 60/135,827 filed May 21, 1999; the disclosures of which applications are herein incorporated by reference.

BACKGROUND OF INVENTION

1. Field of the Invention

The field of the invention is microsurgery, and particularly surgical tools for use therein, and more particularly microsurgical cutting tools.

2. Background of the Invention

Microsurgery is a broad term that refers to any surgical procedures performed under the magnification of a surgical microscope. Microsurgery is being employed to treat an increasing number of conditions, as it provides a number of benefits over conventional surgical techniques. Such advantages include avoidance of complications experienced during conventional, invasive procedures. Furthermore, microsurgery has enabled several new surgical protocols that simply could not be performed on a non-micro scale. As such, microsurgery represents an important, relatively new area of medicine that will continue to gain in applicability in the future. Already, microsurgical techniques are being employed in the areas of opthamology, neurosurgery, laparoscopic surgery, periodontal surgery, reconstructive surgery, reproductive surgery, etc.

Because of the importance of microsurgery to many different fields of medicine, a number of diverse microsurgical tools have been developed. One type of microsurgical tool is a cutting tool, i.e., a tool designed for cutting tissue. Microsurgical cutting tools require precise control of incision size and shape. Microsurgical cutting tools developed to date operate by a variety of different means, including laser means, cavitation means, and the like. For example, localized explosive evaporation and bubble formation generated by optical absorption and breakdown are used in intraocular surgery and other applications for soft tissue cutting and an electric discharge method for creating plasma-induced bubbles has recently been developed.

However, both optical and electric discharge techniques suffer from collateral damage to surrounding tissue. For example, while the vaporization and thermal tissue change due to high plasma temperature are confined to a small area at the probe tip dependent on energy and pulse duration, acoustic transients, bubble expansion and collapse can cause damage far beyond the application site. For example, three-dimensional expansion of the bubble formed inside blood vessels during the laser angioplasty may introduce damage to the walls of the vessel and cause restenosis similarly to the damage introduced during the baloon angioplasty. As discharge energies are reduced to limit collateral damage, the effectiveness of the tool for cutting tissue is also reduced.

As such, there is a continued need for the development of new microsurgical cutting tools that will localize not only the energy deposition but will also spatially confine the subsequent water flow, acoustic transients and other consequences of explosive evaporation. Of particular interest would be the development of a microsurgical cutting tool that provides for one-dimensional (axial) fast pulsating displacement of material with tight radial confinement, which may allow for precise dissection of tissue with minimal collateral damage.

3. Relevant Literature

U.S. patents of interest include: U.S. Pat. Nos. 5,288,288; 5,871,462; 5,944,686 and 6,039,726; as well as the patents reference therein. See also WO 99/33510 and WO 98/12974. Articles of interest include: Palanker, et al., "Dynamics of ArF Excimer Laser-induced Cavitation Bubbles in Gel Surrounded by a Liquid Medium," Lasers in Surgery and Medicine, 21:294–300, 1997; Van Leeuwen, et al., "Excimer Laser Ablation of Soft Tissue: A Study of the Content of Rapidly Expanding and Collapsing Bubbles," IEEE Journal of Quantum Electronics, Vol. 30, No. 5, 1994, pp. 1339–1345; Palanker, et al. "Electric discharge-induced cavitation: A competing approach to pulsed lasers for performing microsurgery in liquid media," Proceedings of the SPIE, Vol. 2975, pp. 351–360; and Alfred Vogel, et al., "Intraocular Nd: YAG Laser Surgery: Light-Tissue Interaction, Damage Range, and Reduction of Collateral Effects," IEEE Journal of Quantum Electronics, Vol. 26, No. 12, 1990, pp. 2240–2260.

SUMMARY OF INVENTION

Microfluidic devices and methods for their use in producing microfluidic jets in a fluid environment are provided. The subject microfluidic devices are characterized by the presence of a microfluid chamber. The microfluid chamber of the subject devices is bounded by at least one opening at a first end, a high pressure producing means opposite the opening, and side walls between the opening and the high pressure producing means. In using the subject devices to produce a microfluidic jet in a fluid environment, the device is contacted with the fluid environment. The pulsed source of high pressure is then actuated in a manner sufficient to increase the pressure in the chamber in a manner sufficient to produce a pulsed microfluidic jet in the fluid environment. The subject devices and methods find use in a variety of different applications, e.g., cutting tissue, introducing fluid into a cell, and the like.

DETAILED DESCRIPTION

Figure 1:
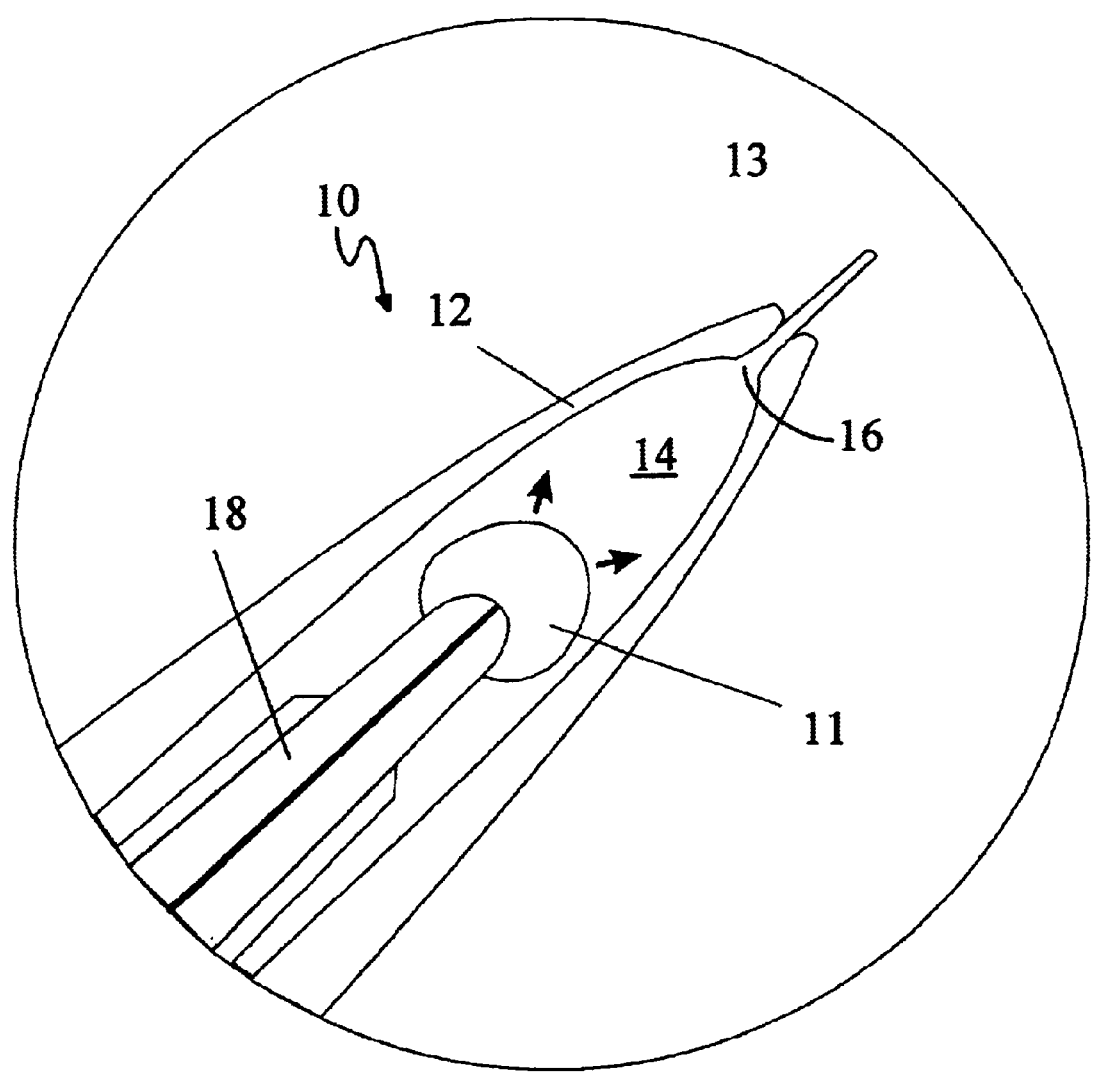
FIG. 1 provides a schematic view of a first embodiment of the subject device, where the device is a micronozzel.

Microfluidic devices and methods for their use in producing microfluidic jets in a fluid environment are provided. The subject microfluidic devices are characterized by the presence of at least one microfluid chamber. The microfluid chamber is bounded by an opening at at least one end, a high pressure producing means opposite the opening, and side walls between the opening and the high pressure producing means. In using the subject devices to produce a microfluidic jet in a fluid environment, fluid is introduced into the chamber, e.g., by contacting the device with the fluid environment in a manner sufficient for fluid to enter the microfluid chamber through the opening or by introducing fluid into the microchamber through a second opening. The high pressure producing means is then actuated in a manner sufficient to increase the pressure in the chamber in a manner sufficient to produce a microfluidic jet in the fluid environment. The subject devices and methods find use in a variety of different applications, e.g., cutting tissue, introducing fluid into a cell, and the like. In further describing the subject invention, the subject devices will be described first in greater detail, both in general terms and in terms of the representative devices depicted in the figures, followed by a review of representative methods in which the subject devices find use.

Devices

As summarized above, the subject invention provides pulsed microfluidic devices that are capable of producing pulsed microjets in a fluid environment. By "microjet" is meant a directed, small diameter, high speed flow of liquid. By directed is meant that the microjet travels in a single direction, i.e., it is unidirectional. By small diameter is meant that the microjets produced by the subject devices have a small diameter, where the diameter typically ranges from about 1 $\mu$m to 1 mm, usually from about 10 $\mu$m to 100 $\mu$m. By high speed is meant that the microjet travels at high velocity, where the velocity of the microjet is generally at least about 10 m/s, usually at least about 50 m/s and more usually at least about 100 m/s.

The subject devices are characterized by the presence of at least one microfluid chamber. The microfluid chambers of the subject devices have at least one opening through which fluid may enter and leave the chamber. In many embodiments, the chambers have a single opening while in other embodiments, 2 or more openings are present, but usually no more than 6 and more usually no more than 4. The openings may be straight or angled, i.e., they may have a central axis that is linear or non-linear, e.g. curvilinear. In certain embodiments, however, the microfluid chambers have a single, straight opening or aperture. In yet other embodiments, the chambers have at least two openings, one for fluid jet ejection and one for fluid entry into the chamber. As such, in certain embodiments, the microfluid chambers are configured such that the opening or aperture is the only way for fluid to enter and leave the chamber. In yet other embodiments, the devices are configured so that fluid can enter into the chamber through a first entry or port and be ejected from the chamber through a second port, opening or aperture.

While the cross-sectional shape of the opening may vary, it is generally at least curvilinear if not circular in shape and has a diameter sufficient to produce a microjet of desired dimension and properties, as described above. In many embodiments, the diameter of the opening ranges from about 1 $\mu$m to 1 mm, usually from about 10 $\mu$m to 100 $\mu$m.

The volume of the microfluid chamber is sufficient to produce the desired microjet upon actuation of the pressure producing means, as described infra. The volume of the microfluid chamber typically ranges from about 10 $\mu$m$^3$ to 1 cm$^3$, usually from about 100 $\mu$m$^3$ to 1 mm$^3$ and more usually from about 1000 $\mu$m$^3$ to 0.1 mm$^3$. The configuration of the microchamber may vary depending on the particular design of the device, but in many embodiments is generally substantially conical in shape, with the opening positioned at the apex of the cone. See the representative embodiments shown in the figures and described in greater detail infra.

Located in the microfluid chamber is a pressure producing means, where the pressure producing means is a means sufficient to increase the pressure inside of the microfluid chamber at a sufficient rate and by a sufficient amount to produce the microjet. Any convenient pressure producing means may be present in the subject microfluid chambers, so long as the pressure producing means is capable of producing a pressure increase in the microfluid chamber sufficient to produce a microjet, as described above. The pressure producing means may be located in any convenient location of the chamber, but is generally at the floor of the chamber positioned opposite the opening of the chamber. In general, the pressure producing means should be a means that is capable of raising the pressure inside the microfluid chamber by a sufficient magnitude in a sufficiently short period of time to produce a microjet of the desired properties, as described above. In many embodiments, the pressure producing means is one that is capable of raising the pressure by a magnitude of at least about 10 Bar, usually at least about 100 Bar in a period of time that does not exceed about 10 ms and usually does not exceed about 100 $\mu$s, such that a pressure ranging from about 1 Bar to 1000 Bar, usually from about 10 to 100 Bar is produced in the microfluid chamber in a period of time ranging from about 1 $\mu$s to 10 ms, usually from about 10 $\mu$s to 100 $\mu$s. Representative pressure producing means of interest include, but are not limited to: pump means, e.g., reciprocating or peristaltic pump means, such as piezoelectrically-driven flexible membranes; bubble producing means, e.g., optical breakdown, optical absorption, electric breakdown, Joule heating, acoustic bubble formation etc.; and the like.

Of particular interest in the subject devices are vapor producing means, where the vapor producing means are capable of producing a vapor bubble inside the microfluid chamber that results in the production of the microjet. Any convenient vapor bubble producing means capable of producing a vapor bubble inside of the chamber from the fluid present therein may be employed. In many embodiments the vapor bubble producing means is a high pressure producing means capable of delivering energy to the fluid present in the chamber whereby the vapor bubble is produced which creates high pressure in the fluid chamber. Representative high energy vapor bubble producing means include: electric breakdown means, laser means, joule heating and resistance heating means, and the like.

The subject devices may include a single microfluid chamber or a plurality of microfluid chambers, where by plurality of microfluid chambers is meant at least 2, usually at least 4 and more usually at least 10 microfluid chambers, where in certain embodiments the devices include an array of at least about 50, usually at least about 100 and more usually at least about 1000 or more microfluid chambers, where the chambers are generally arranged in the form of pattern or grid, as described in the representative embodiment supra. See FIG. 2.

The subject devices may be configured in a variety of different ways depending upon the use of the device. For example, where the device is a microsurgical cutting device, the device may have an elongated configuration with the microfluid chamber present at one end. The elongate configuration may be made up of an elongate tube, that may be rigid or flexible, as necessary or desirable for accessing the site of the fluid environment in which the fluidic jet is to be created. For example, in certain embodiments, the microfluid chamber will be at the end of a rigid elongate tube or analogous structure that provides for handling and positioning of the device, where the tube will be at least about 3 cm long, usually at least about 5 cm long and more usually at least about 10 cm long, and may be much longer. In those embodiments where the tube is a flexible tube, it will have a length of analogous catheter devices, and be connected at the proximal end to standard catheter controlling means, where such means are well known in the art. Alternatively, where the device is designed for injecting fluid into a cell, the device may include a cell holder above the microfluid chamber for receiving the microjet. Representative device configurations are described further in terms of the figures, infra.

In addition to the at least one microfluid chamber, as described above, the subject devices further include a means for actuating the pressure producing means. The means for actuating the pressure producing means necessarily varies depending on the nature of the pressure producing means. For example, where the pressure producing means is a vapor bubble producing means, the actuating means may be any means of turning on the vapor bubble producing means to produce a vapor bubble in the chamber, e.g., a means for providing electrical current to the producing means.

Figure 3:
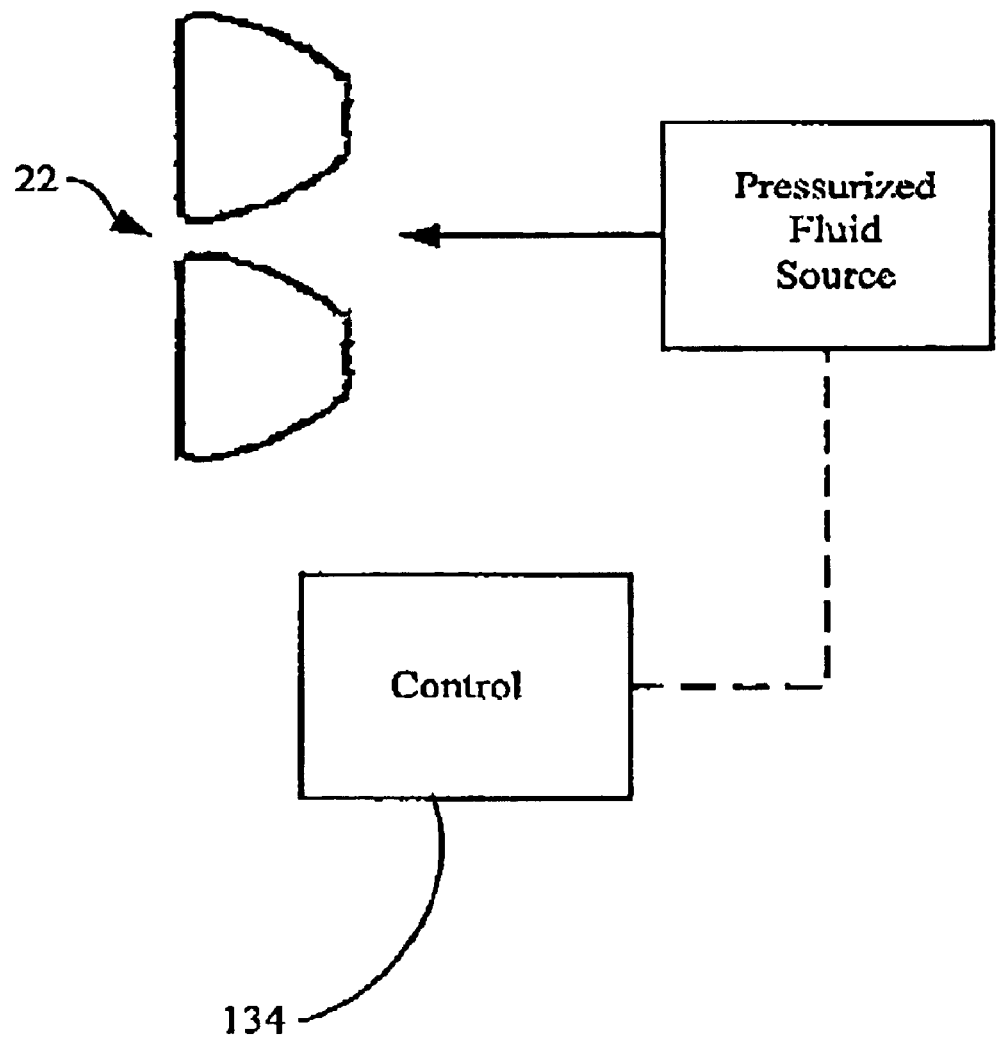
FIG. 3 provides a schematic view of a device including a control according to an embodiment of the present invention.

As shown in FIG. 3, in one embodiment of the invention microfluidic device 10 further includes a control 134 that serves as means for actuating the pressure producing means to produce a pressurized fluid source communicating with, for example, nozzle(s) 22. Control 134 may be programmed by a person of ordinary skill in the art to provide preferred delivery pressures, velocities, and frequencies as described herein below.

In certain embodiments of the subject devices, the devices do not include a fluid communication means to a fluid reservoir. In other words, the microfluid chambers have no openings or passages that provide for fluid communication between the chamber and a fluid reservoir. As such, the only way for fluid to enter and leave the microfluid chamber in these embodiments of the device is via the opening through which the microfluid jet emerges upon actuation of the device. In yet other embodiments, the chambers have one or more additional openings through which fluid may enter the chamber, where these fluid entry openings are preferably high impedance openings through which the fluid jet produced by the increase in pressure does not exit but which allow fluid to slowly enter the chamber following firing of a jet.

The subject devices will now be described in greater detail in terms of the figures. FIG. 1 provides a schematic diagram of a representative catheter device according to the subject invention that has a micronozzle configuration. The device 10 comprises micronozzel 12. The micronozzel 12 houses the microfluid chamber 14, which microfluid chamber is characterized by the presence of a single aperture or opening 16. The chamber has an access for liquid from the back side (between the electrode and the chamber walls). The microfluid chamber has a volume ranging from about 1 $\mu m^3$ to 1 $mm^3$, usually from about 10 $\mu m^3$ to 100 $\mu m^3$ and the aperture or opening 16 has a diameter ranging from about 1 $\mu m$ to 1 mm, usually from about 10 $\mu m$ to 100 $\mu m$. Positioned opposite the aperture or opening is electrode vapor bubble producing means 18. The electrode is typically a high voltage electrode made up of a suitable material, e.g., metal wire embedded in insulator and the like. The distance between the electrode and the aperture typically ranges from about 1 $\mu m$ to 10 mm, usually from about 10 $\mu m$ to 1 mm. As can be seen in FIG. 1, the nozzle has a conical configuration with the aperture or opening positioned at the apex of the cone and the electrode positioned at the bottom of the cone. The inner diameter of the cone gradually increases from the apex to the base and may range from about 1 $\mu m$ to 1 mm , usually from about 10 $\mu m$ to 100 $\mu m$, where the angle between the side walls typically ranges from about 5 degrees to 50 degrees, usually from about 10 degrees to 30 degrees. The physical characteristics and dimensions of the micronozzel are chosen to provide for a microjet of desired properties, as the properties of the microjet produced by the subject nozzles depend, at least in part, on the nozzle dimensions, e.g., taper angle, aperture size, nozzle length, and the like. To further tailor the nature the microjet produced by the subject devices, the nozzle may be curved.

Figure 2A:
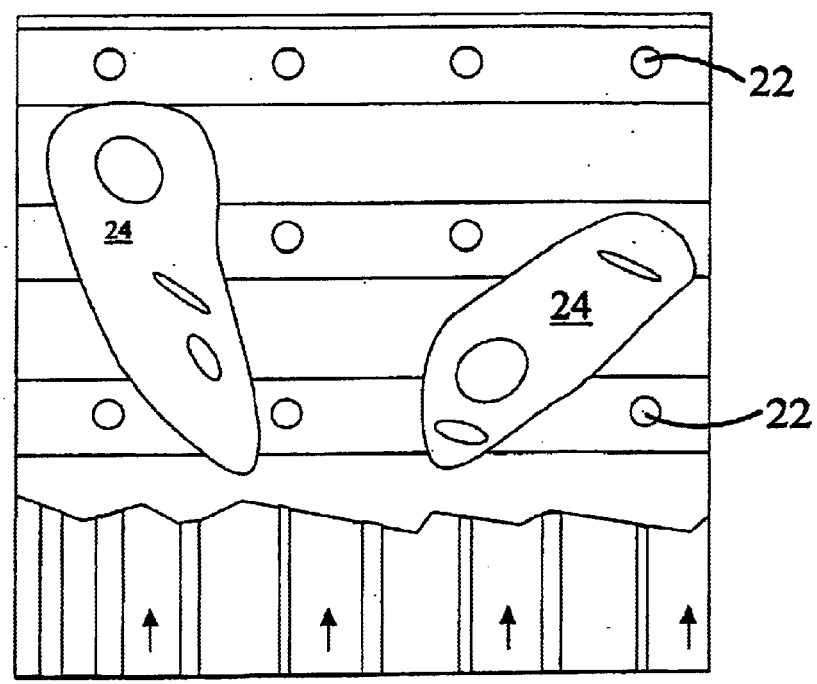
FIGS. 2A & 2B provide a schematic view of a second embodiment of the subject device, where the device is an array of individually actuatable microfluid chambers.
Figure 2B:
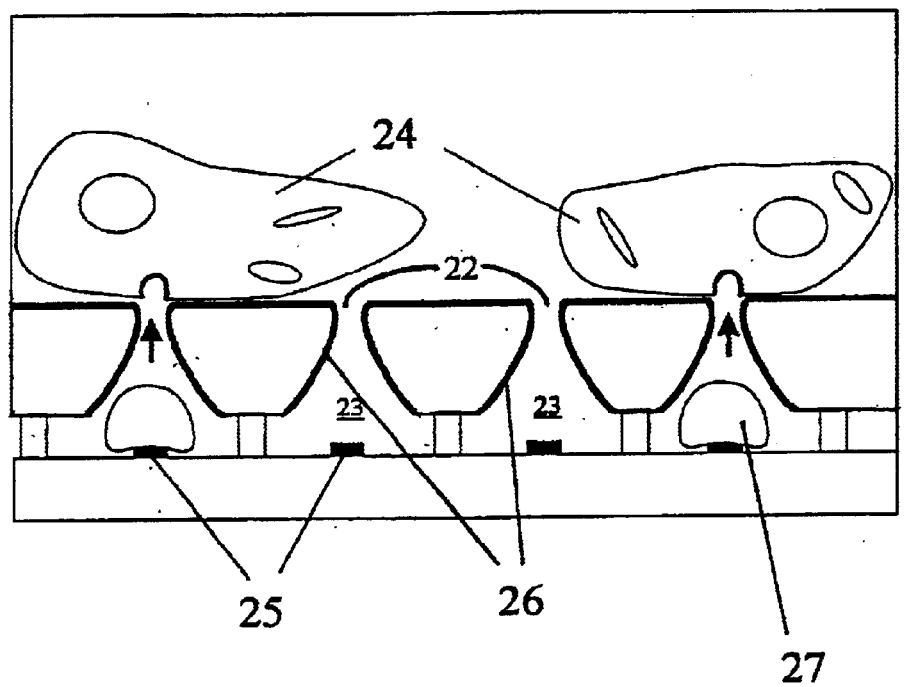

FIGS. 2A and 2B provide a schematic view of a second embodiment of the subject device, in which a plurality of microfluid chambers are arranged across the surface of a substrate to form an array of microfluid chambers. FIG. 2A provides an overhead view of the device showing two cells 24 positioned on the surface of the array and a plurality of openings 22, while FIG. 2B provides a cross-sectional view of the device shown in FIG. 2A. In other words, the device shown in FIG. 2 is an array of a microfluid chambers. In the device shown in FIG. 2, the array 20 is made up of substrate 21 on which a plurality of different microfluid chambers 23 are arranged in a grid or analogous pattern. Each microfluid chamber 23 has a volume ranging from about 10 $\mu m^3$ to 1 $cm^3$, usually from about 100 $\mu m^3$ to 1 $mm^3$ and more usually from about 1000 $\mu m^3$ to 0.1 $mm^3$. Each microfluid chamber is conical shaped, having an aperture 22 at the apex and a vapor producing means 25, e.g., an electrode, on the floor. In the representation shown in FIG. 2B, the electrode 25 is an anode and the cathodes 26 are positioned on the side walls of the chamber. The diameter of the aperture 22 typically ranges from about 1 $\mu m$ to 1 mm, usually from about 10 $\mu m$ to 100. The distance between the aperture and the floor of the chamber typically ranges from about 10 $\mu m$ to 1 cm, usually from about 100 $\mu m$ to 1 mm. Also shown in FIG. 2A is vapor bubble 27 which is causing fluid to be injected into cell 24 through opening 22. The individual microfluid chambers of the array are generally individually actuatable.

The subject devices may be fabricated from any convenient material or materials, where representative materials include polymers and plastics, glasses, metals, etc. The subject devices may be fabricated using any convenient methodology, where suitable fabrication protocols include machining, molding, microfabrication and the like. A representative fabrication protocol is provided in the experimental section, infra .

Methods

Also provided are methods of using the subject devices to produce a microfluidic jet in a fluid environment. To produce a microfluidic jet in a fluid environment according to the subject methods, fluid is first introduced into the microfluid chamber. In many embodiments, fluid is introduced into the microfluid chamber by contacting the device with the fluid environment and air within the device is removed in a manner sufficient for fluid to enter the microfluid chamber of the device through the aperture, or other entry port(s). The manner of contact and air removal may vary depending on the particular configuration and nature of the device. For example, where the device is in the form of a single micronozzel, e.g., positioned at the end of an elongated structure as shown in FIG. 1, such as a catheter or tube, contact typically includes at least submersing the micronozzel portion of the device in the fluid environment in which the microjet is to be produced and drawing fluid in through the tip. Air may also be removed and fluid drawn into the device by a second hole in the device that is then sealed or otherwise unused during operation of the device, e.g. where the hole or opening may be a low impedance opening that prevents pressure from causing a microfluid jet to exit through it. Alternatively, where the device is an array of microfluid chambers as shown in FIG. 2, contact is achieved by placing the fluid environment onto the surface of the array, e.g., by flooding the surface of the array with the fluid environment.

The subject methods are suitable for producing microfluidic jets in a variety of different fluid environments. Fluid environments of interest are generally those made up of aqueous fluids, e.g., pure water, water and one or more solutes, e.g., salts, buffers, and the like.

Following filling of the microfluid chamber with fluid through the aperture, e.g., through contact of the opening of the microfluid chamber with the fluid environment, the device is actuated while maintaining contact with the fluid environment in a manner sufficient to produce the microjet in the fluid environment. By actuation of the device is meant actuation of the pressure producing means at least once in a manner sufficient to produce a microjet of fluid in the fluid environment, where the microfluidic jet originates at the aperture of the micronozzel. The manner in which the pressure producing means is actuated necessarily depends on the nature of the actuation means. For example, where the pressure producing means is an electrode, actuation includes delivering electric current to the electrode. Likewise, where the pressure producing means is an optical fiber, actuation includes delivering light to the fiber.

The pressure producing means is actuated in a manner sufficient to produce a pressure change in the microfluid chamber that is sufficient to produce the microfluidic jet. Generally, the pressure producing means is actuated in a manner sufficient to increase the pressure in the microfluid chamber by at least about 10 Bar, usually at least about 100 Bar in a period of time that does not exceed about 10 ms and usually does not exceed about 100 $\mu$s, such that a pressure ranging from about 1 Bar to 1000 Bar, usually from about 10 to 100 Bar is produced in the microfluid chamber in a period of time ranging from about 1 $\mu$s to 10 ms, usually from about 10 $\mu$s to 100 $\mu$s.

In many embodiments, the pressure producing means is actuated in a manner that produces a pulsed microjet. By pulsed microjet is meant a microjet that is periodic, i.e., not constant. By periodic is meant that there are gaps or spaces in the microjet. An analogous concept is the pulsed laser, where such devices are described in WO 98/12974, the disclosure of which are herein incorporated by reference. Where the produced microjet is pulsed, the periodicity of the microjet may vary, where by "periodicity" is meant that time period duration from one pulse to the next. Generally, the periodicity of the pulsed microjet in terms of number of pulses for a given period of time ranges from about 0.1 Hz to 10 kHz, usually from about 1 Hz to 1 kHz and more usually from about 10 Hz to 100 Hz. The manner in which the pressure producing means is actuated to achieve the pulsed microjet necessarily depends on the nature of the pressure producing means. For example, where the pressure producing means is an electrode, discharges or bursts of electric current are provided to the electrode in order to produce a periodic bubble in the microfluid chamber, where the periodicity of the bursts mirrors the periodicity of the pulsed microjet, and generally ranges from about 0.1 Hz to 10 kHz, usually from about 1 Hz to 1 kHz. The amplitude of a given discharge typically ranges from about 1 $\mu$J to 1 J, usually from about 10 $\mu$J to 10 mj.

As described above, actuation of the pressure producing means in the microfluid chamber results in the production of a microjet exiting the microfluid chamber through the aperture and entering the fluid environment in which the micronozzel is present. The speed of the ejection may vary and is directly proportional to the speed at which rate at which the pressure increases in the microfluid chamber. Typically the speed of the ejection ranges from about 1 m/s to 100 m/s, usually from about 10 m/s to 50 m/s. At high ejection speeds, a cavitation bubble forms at the aperture of the micronozzle, where the cavitation bubble typically forms at speeds in excess of at least about 30 m/s and usually at least about 40 m/s. In certain applications, formation of the cavitation bubble at the aperture is desirable. Thus, the subject devices can be operated in a low velocity mode that produces microfluidic jets without cavitation bubbles and a high velocity mode that produces microfluidic jets accompanied by cavitation bubbles. Where a cativation bubble is produced, the bubble is produce by fluid vapor which is ejected from the microfluid chamber. In these situations, the fluid jet is actually a fluid vapor jet, and the definition of the term fluid jet in this specification should be read to include both jets made of liquid and jets made of vapor, i.e., fluid vapor jets.

Utility

The above described devices and methods find use in a variety of different applications. One type of application in which the subject devices and methods find use is in the manipulation of organic masses, e.g., tissue, clots, etc., in microsurgical applications. By manipulation of organic mass is meant the physical alteration of the organic mass. Specific examples of how the device may be employed to manipulate organic masses include, cutting tissue, drilling holes or channels in tissue, disrupting and dispersing clots, and the like.

With respect to tissue cutting, the subject methods and devices find use in clot disintegration for stroke treatment and angioplasty (removal of occlusions in blood vessels). When used to cut tissue, the distance between the aperture and the tissue may vary, where the distance typically ranges from about 0 to 10 mm, usually from about 0 to 1 mm, and may be chosen to reduce collateral damage while retaining effective tissue cutting. The subject devices may also be used for treatment of vein occlusions to "massage" veins by the water flow pushing the clots downstream without introduction of the device inside the blood vessel.

The subject methods and devices also find use in the introduction of fluid into small objects, e.g. cells and the like. In such applications, the fluid which is introduced into the microfluid chamber is the fluid that is desired to be introduced into the object. The object is placed over the aperture and the device is actuated to produce the microjet of fluid that enters the object, thereby introducing fluid into the object. In these embodiments, the distance between the object and the aperture generally ranges from about 0 to 100 $\mu$m, usually from about 0 to 10 $\mu$m . Applications where this particular type of protocol finds use include delivery of macromolecules into cells such as proteins, DNA and the like.

The above described applications are merely representative, and by no means exhaustive, of the various disparate applications in which the subject methods and devices find use.

The following examples are offered by way of illustration and not by way of limitation.

EXPERIMENTAL

I. Pulsed Liquid Microjet

A. Fabrication

The micronozzle is fabricated from borosilicate glass or quartz. A capillary tube is heated by a $CO_2$ laser and pulled in a pipette-pulling instrument to give the desired taper and wall thickness. The tapered tube is polished to open the exit hole of the aperture. Under a microscope, the tip of the polished nozzle is heated to thicken the exit hole walls and reflow the glass to the desired exit hole size. The nozzle is mounted and secured over a high-voltage electrode the size of a hypodermic needle that provides the rapid pressure pulse. Prior to use, the nozzle must be filled with a solution, such as saline, which is ejected during a pressure pulse.

B. Testing

A small-diameter hole is produced in a gel to simulate tissue cutting. A pulsed liquid microjet as described above, with the nozzle mounted on a high-voltage electrode, is filled with saline solution. A gel is immersed in saline and the tip of the microjet is brought in close proximity to the gel surface. The high-voltage electrode is fired, creating a spherical bubble within the nozzle due to fast overheating of the saline. Pressure from the bubble expansion drives fluid through the nozzle exit hole in a confined, uni-directional flow. The liquid jet impinges on the gel and bores a small hole approximately the size of the nozzle exit hole. Repeated firing of the jet increases the depth of the cut but not the width. At high pressures, the high-speed flow from the nozzle creates a cavitation bubble at the exit hole. The bubble can be used for cutting larger areas more quickly than the liquid jet.

It is evident from the above description and results that the subject methods and devices represent a significant improvement in the area of microsurgical tools, particularly microsurgical cutting tools. The pulsed liquid microjet device of the subject invention offers three distinct improvements over existing methods of tissue cutting. Using the subject methods and devices, collateral damage is reduced in the radial direction by converting the three-dimensional expansion of a cavitation bubble into a one-dimensional flow of a liquid or vapor jet. Acoustic transients resulting from expansion and collapse of the bubble are damped by the nozzle. In addition, the one-dimensional jet created by the pulsed microjet extends the cutting action away from the probe tip, allowing greater separation between the probe and application area and thus allowing dissection and treatment of tissue without direct contact with it by the instrument. Furthermore, high-energy discharges, which would cause unacceptable collateral damage with existing systems, can be used in the pulsed liquid microjet to create more efficient and effective soft tissue cutting and to extend applicability those techniques to more dense tissues. Use of the pulsed liquid microjet for clot disruption in veins and arteries would take advantage of one-dimensional flow and protection from collateral damage. Application of the technology to fluid injection would benefit from the high-speed, directed flow and well-defined volume of the injected material. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for producing a microfluid jet in a fluid environment, said device comprising:
a microfluid chamber having:
(i) at least one opening at a distal end;
(ii) a vapor producing means opposite said opening;
wherein said fluid chamber is capable of producing a microfluidic jet in a fluid environment upon actuation; and
a control configured to control actuation of said vapor producing means and thereby increase pressure within said microfluid chamber to accelerate the microfluidic jet to a velocity of at least about 30 meters per second.

2. The device according to claim 1, wherein said vapor producing means produces a vapor bubble inside said microfluid chamber.

3. The device according to claim 1, wherein said vapor producing means is a high pressure vapor producing means.

4. The device according to claim 3, wherein said high pressure vapor producing means is an electrode.

5. The device according to claim 3, wherein said high pressure vapor producing means is a laser.

6. The device according to claim 1, wherein said opening has a diameter ranging from about 1 $\mu$m to 1 mm.

7. The device according to claim 1, wherein a distance of 1 $\mu$m to 1 cm separates said opening and said oppositely positioned vapor producing means.

8. A device for producing a microfluidic jet in a fluid environment, said device comprising:
a micronozzle having a distal end comprising a fluid chamber, wherein said fluid chamber has a volume ranging from about 10 $\mu$m$^3$ to 1 cm$^3$ and comprises:
(i) a single opening having a diameter ranging from about 1 $\mu$m to 1 mm;
(ii) a vapor producing means located opposite said opening and separated from said opening by a distance ranging from about 1 $\mu$m to 1 cm;
wherein said fluid chamber is capable of producing a microfluidic jet in a fluid environment upon actuation; and
a control configured to control said actuation of said vapor producing means such that the microfluidic jet is accelerated to a velocity of at least about 30 meters per second.

9. The device according to claim 8, wherein said vapor producing means is a high pressure vapor producing means capable of introducing energy into a fluid in a manner sufficient to produce a vapor bubble.

10. The device according to claim 9, wherein said high pressure vapor producing means comprises an electrode.

11. The device according to claim 9, wherein said vapor producing means comprises a laser.

12. The device according to claim 8, wherein said opening has a diameter ranging from about 1 $\mu$m to 1 mm.

13. A device for producing a microfluidic jet in a fluid environment, said device comprising:
a micronozzle having a distal end comprising a fluid chamber, wherein said fluid chamber has a volume ranging from about 10 $\mu$m$^3$ to 1 cm$^3$ and comprises:
(i) a single opening having a diameter ranging from about 1 $\mu$m to 1 mm;
(ii) an electrode vapor producing means located opposite said opening and separated from said opening by a distance ranging from about 10 $\mu$m to 1 cm;
wherein said fluid chamber is capable of producing a microfluidic jet in a fluid environment upon actuation; and
a controls configured to generate a signal wherein said signal controls actuation of said vapor producing means such that fluid in said micronozzle is expelled from said micronozzle at a velocity of not less than about 30 meters per second.

14. A device comprising at least two microfluid chambers, wherein each microfluid chamber comprises:
    (i) an opening at a distal end; and
    (ii) a vapor producing means opposite said opening;
    wherein each of said microfluid chambers is capable of producing a microfluidic jet in a fluid environment upon actuation;
    a control configured to generate a signal, wherein said signal controls actuation of said vapor producing means such that fluid in said micronozzle is expelled from said micronozzle at a velocity of not less than about 30 meters per second.

15. The device according to claim 14, wherein said at least two microfluid chambers are individually actuatable.

16. The device according to claim 14, wherein said device comprises a plurality of said microfluid chambers.

17. The device according to claim 16, wherein said device comprises an array of microfluid chambers.

18. A method of producing a fluid microjet in a fluid environment, said method comprising:
    (a) contacting said fluid environment with a microfluid chamber comprising:
        (i) an opening at a distal end; and (ii) a vapor producing means opposite said openings; and
    (b) actuating said vapor producing means in a manner sufficient to produce a vapor bubble inside said fluid chamber; whereby a fluid microjet is produced in said fluid environment; and
    controlling actuation of said vapor producing means such that the microfluidic jet is accelerated to a velocity of at least about 30 meters per second.

19. The method according to claim 18, wherein said vapor producing means is actuated in a manner sufficient to produce pulsed microfluid jets in said fluid environment.

20. The method according to claim 18, wherein said microfluid chamber is positioned proximal to a tissue in said fluid environment and said method is a method of physically modulating said tissue with said fluid microjet.

21. The method according to claim 20, wherein said method is a method of cutting tissue.

22. The method according to claim 20, wherein said micronozzel is positioned proximal to a cell and said method is a method of introducing fluid into said cell.

23. The method according to claim 20, wherein said micronozzel is positioned proximal to a blood vessel and said method is a method of manipulating a clot by a water jet.

24. The device of claim 1, wherein said control controls actuation of said vapor producing means to accelerate the microfluidic jet to a velocity of at least about 40 meters per second.

25. The device of claim 1, wherein said control controls actuation of said vapor producing means to accelerate the microfluidic jet to a velocity of at least about 50 meters per second.

26. The device of claim 1, wherein said control controls actuation of said vapor producing means to accelerate the microfluidic jet to a velocity of at least about 100 meters per second.

27. The device of claim 1, wherein said control controls actuation of said vapor producing means such that the pressure in said microfluid chamber increases to at least about 10 Bar.

28. The device of claim 1, wherein said control controls actuation of said vapor producing means such that the pressure in said microfluid chamber increases to at least about 100 Bar.

29. The device of claim 1, wherein said control controls actuation of said vapor producing means such that the pressure in said microfluid chamber increases from about 1 Bar to 1000 Bar.

30. The device of claim 1, wherein said control controls actuation of said vapor producing means such that the pressure in said microfluid chamber increases from about 10 Bar to 100 Bar.

31. The device of claim 1, wherein said control controls actuation of said vapor producing means such that the pressure in said microfluid chamber increases over a period of time from about 10 micro seconds to 100 micro seconds.

32. The device of claim 1, further comprising at least one anode and at least one cathode.

33. The device of claim 32, wherein said cathode is positioned on a side wall of said microfluid chamber.

34. The device of claim 32, wherein said cathode is configured to be at least a portion of a side wall of said chamber.

35. The device of claim 1, wherein said control controls actuation of said vapor producing means such that the pressure in said microfluid chamber increases over a period of time from about 1 micro seconds to 10 milliseconds.

* * * * *